US00PP34540P2

(12) United States Plant Patent
Krebs

(10) Patent No.: US PP34,540 P2
(45) Date of Patent: Sep. 6, 2022

(54) ***RHODODENDRON* PLANT NAMED 'HOLDENRHODO213'**

(50) Latin Name: *Rhododendron hybrida*
Varietal Denomination: HoldenRhodo213

(71) Applicant: Holden Forests and Gardens, Kirtland, OH (US)

(72) Inventor: Stephen Krebs, Painesville, OH (US)

(73) Assignee: HOLDEN FORESTS AND GARDENS, Kirtland, OH (US)

( * ) Notice: Subject to any disclaimer, the term of this patent is extended or adjusted under 35 U.S.C. 154(b) by 0 days.

(21) Appl. No.: 17/562,231

(22) Filed: Dec. 27, 2021

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238, 239
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Rhododendron* plant named 'HoldenRhodo213' that is characterized by its resistance to root rot caused by *Phytophthora cinnamomi*, its cold hardiness at least in U.S.D.A Zone 5a, its flower buds that are pink in color that open to flowers that are creamy white in color with yellow centers, and its adaptability to open field conditions in Northeast Ohio with soil pH up to at least 6.2.

2 Drawing Sheets

Botanical classification: *Rhododendron hybrida.*
Cultivar designation: 'HoldenRhodo213'.

BACKGROUND OF THE INVENTION

The present invention relates to a new and distinct cultivar of *Rhododendron* plant of hybrid origin, botanically known as *Rhododendron* 'HoldenRhodo213' and will be referred to hereafter by its cultivar name, 'HoldenRhodo213'. 'HoldenRhodo213' is a new cultivar of *Rhododendron* shrub grown for use as a landscape plant.

The new cultivar arose from a controlled breeding program by the Inventor in Madison, Ohio and Kirtland, Ohio with the objective of developing new cultivars of *Rhododendron* with resistance to root rot, great sun adaptability, and compact growth habits.

The new cultivar was derived from a cross made by the Inventor in spring of 1997 between *Rhododendron* 'Golden Gala' (not patented) as the female parent, and *Rhododendron* 'Rio' (not patented) as the male parent. The Inventor selected 'HoldenRhodo213' as a single unique plant amongst the seedlings that resulted from the above cross in winter of 1999.

Asexual propagation of the new cultivar was first accomplished by semi-hardwood stem cuttings in Madison, Ohio in fall of 2007 under the direction of the Inventor. Asexual propagation by semi-hardwood stem cuttings and tissue culture utilizing meristematic tissue has determined that the characteristics of the new cultivar are stable and are reproduced true to type in successive generations.

SUMMARY OF THE INVENTION

The following traits have been repeatedly observed and represent the characteristics 'HoldenRhodo213'. These attributes in combination distinguish 'HoldenRhodo213' as a new and distinct cultivar of *Rhododendron.*

1. 'HoldenRhodo213' exhibits resistance to root rot caused by *Phytophthora cinnamomi.*
2. 'HoldenRhodo213' exhibits cold hardiness at least in U.S.D.A Zone 5a.
3. 'HoldenRhodo213' exhibits flower buds that are pink in color that open to flowers that are creamy white in color with yellow centers.
4. 'HoldenRhodo213' exhibits adaptability to open field conditions in Northeast Ohio with soil pH up to at least 6.2.

The female parent of 'HoldenRhodo213' differs from 'HoldenRhodo213' in having flowers that are uniformly pale yellow in color with a subtle nectar guide. The male parent of 'HoldenRhodo213' differs from 'HoldenRhodo213' in having mature flowers that are pink in color with yellow centers. 'HoldenRhodo213' can also be most closely compared to the *Rhododendron* cultivars 'Percy Wiseman' (not patented) and 'Capistrano' (not patented). 'Percy Wiseman' is similar to 'HoldenRhodo213' in having a compact plant habit and a similar flower coloration. 'Percy Wiseman' differs from 'HoldenRhodo213' in being less cold hardy (to U.S.D.A. Zone 6) and susceptible to root rot. 'Capistrano' is similar to 'HoldenRhodo213' in cold hardiness, growth rate and plant habit. 'Capistrano' differs from 'HoldenRhodo213' in being susceptible to root rot and in having flowers that are yellow in color.

BRIEF DESCRIPTION OF THE DRAWINGS

The accompanying color photographs illustrate the overall appearance and distinct characteristics of the new *Rhododendron*. The plant in the photographs is 6 years in age as grown outdoors in Kirtland, Ohio.

The photograph in FIG. 1 provides a view of 'HoldenRhodo213' in bloom.

Figure 1:
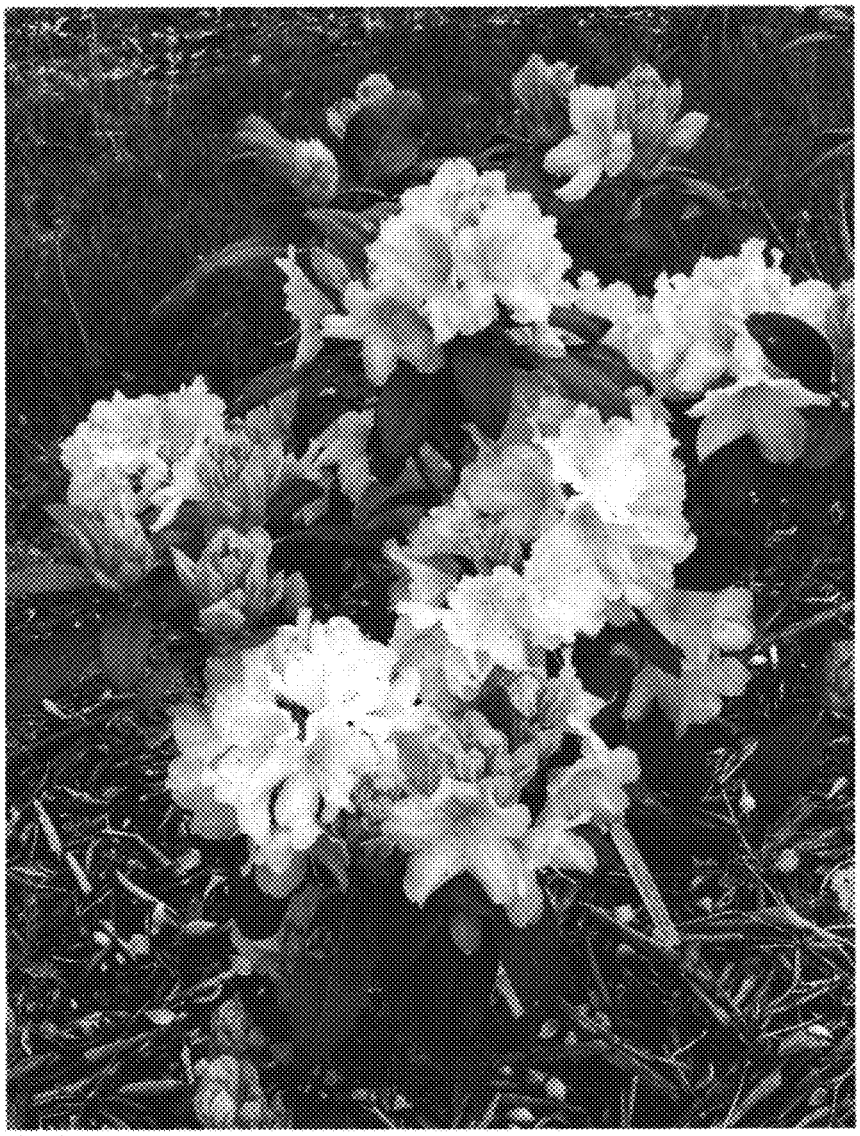
Figure 2:
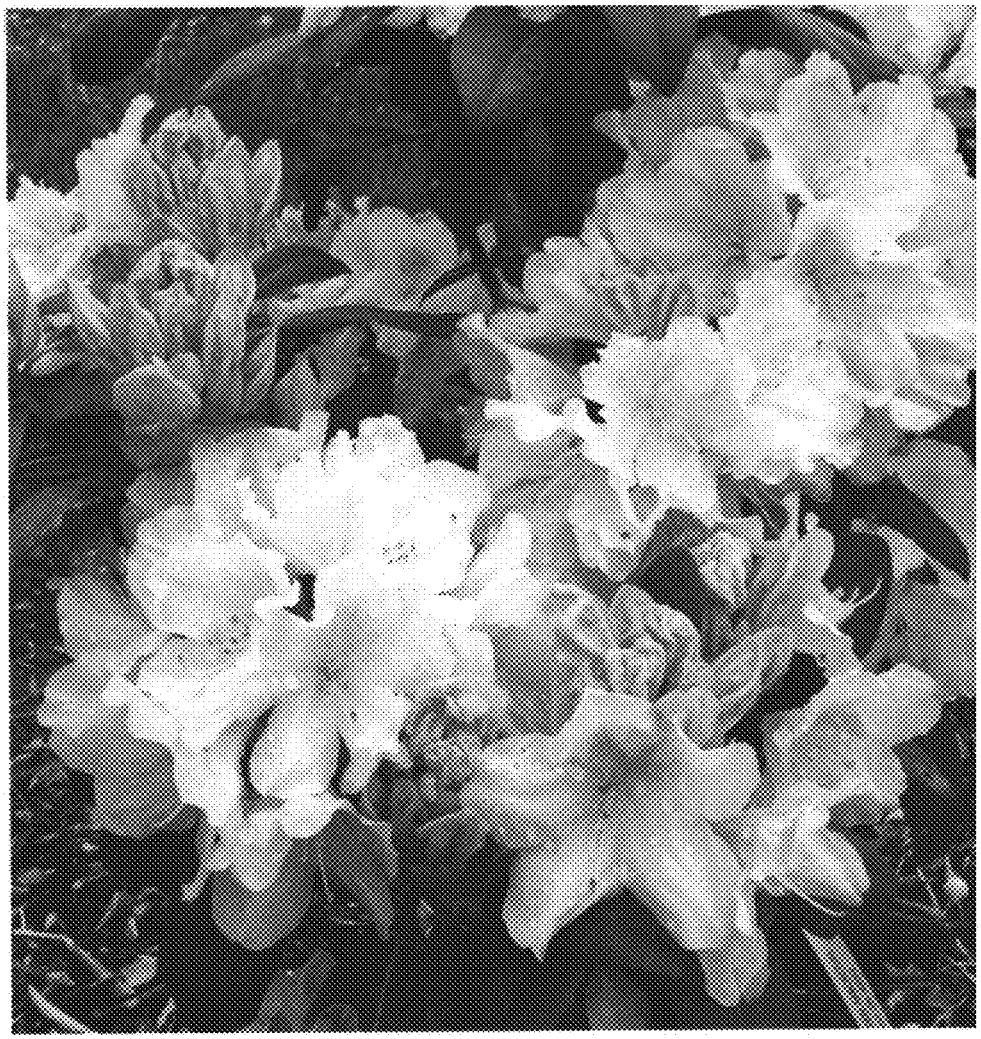

The photograph in FIG. 2 provides a close-up view of the inflorescences and flower buds of 'HoldenRhodo213'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of a 9-year-old plant of the new cultivar as grown outdoors in an evaluation garden in Madison, Ohio. The phenotype of the new cultivar may vary with variations in environmental, climatic, and cultural conditions, as it has not been tested under all possible environmental conditions. The color determination is in accordance with The 1995 Colour Chart of The Royal Horticultural Society, London, England, except where general color terms of ordinary dictionary significance are used.

General characteristics:

*Blooming period.*—2 to 3 weeks dependent on weather, typically commencing in mid-May in Ohio.

*Plant type.*—Evergreen shrub.

*Plant habit.*—Rounded and densely branched.

*Height and spread.*—Reaches 84 cm in height and 77 cm in width after 9 years in the landscape.

*Cold hardiness.*—Plant is hardy to at least U.S.D.A. Zone 5a, flower buds are resistant to cold damage when exposed to temperatures of −20 F, possibly colder.

*Diseases and pests.*—Observed to be resistant to root rot caused by *Phytophthora cinnamomi* under field conditions, typical of evergreen rhododendrons; lace bugs (*Stephanitis takeyai*) can establish on leaves under full sun conditions, no other susceptibility or resistance to other pests or diseases has been observed.

*Root description.*—Fibrous and 165A in color.

*Propagation.*—Tissue culture (preferred) or semi-hardwood stem cuttings.

*Growth rate.*—Moderate.

*Root development.*—4 to 8 weeks for root initiation from an unrooted cutting, 2 years to produce a young plant from a rooted cutting.

Stem description:

*Shape.*—Round.

*Stem color.*—Young growth is near 144B, gradually transitioning to 138A and then 151A, mature stems; a blend of 156A and 176A.

*Stem size.*—Main stems; 10.1 cm length and 2.2 cm in width, lateral branches; 77.9 cm in length and 1.4 cm in width, current season growth; an average 5.1 cm in length and 4 mm in width.

*Stem surface.*—Young growth is slightly rough to the touch, moderately covered in wooly pubescent hairs, mature surface is rugose and glabrous.

*Stem aspect.*—Held outward from main stem.

*Stem strength.*—Strong.

*Branching.*—Densely branched; degree dependent on pruning.

Foliage description:

*Leaf shape.*—Elliptic to obovate.

*Leaf division.*—Simple.

*Leaf base.*—Obtuse to mildly acute.

*Leaf apex.*—Acute to obtuse.

*Leaf venation.*—Pinnate, upper surface; 144B and 145A in color, lateral vein colors match leaf color, lower surface; midrib and lateral veins 144C and 138B in color.

*Leaf margins.*—Entire.

*Leaf attachment.*—Petiolate.

*Leaf arrangement.*—Alternate, leaf clusters whorled at shoot apex.

*Leaf internode length.*—Up to 5.5 cm, decreasing to 0 cm where leaves are whorled at the apex.

*Leaf orientation.*—Held nearly parallel to the ground to drooping between angles of 30° to 45° downward.

*Leaf aspect.*—Leaves mostly flat with occasional cupping or twisting near the tip.

*Leaf surface.*—Upper surface; smooth, glabrous, mildly shiny with a thick texture, lower surface; smooth, dull, glabrous.

*Leaf color.*—Young leaves upper surface; 146A, young leaves lower surface; 146D, mature leaves upper surface; a blend of 147C and 139A, mature leaves lower surface; 147D, older leaves; evergreen, same color as mature leaves in fall but occasionally yellow and drop in fall.

*Leaf size.*—Ranging from 3.3 to 12.5 cm in length and 2.2 to 4.7 cm in width.

*Leaf quantity.*—An average of 5 leaves per current season shoot.

*Petioles.*—Average of 1.3 cm in length and 2 mm in diameter, near 150B in color, smooth and lightly granular pubescent surface.

Flower description:

*Inflorescence type.*—Umbellate raceme.

*Lastingness of flowers.*—Last 2 to 3 weeks weather depending, flower petals self-cleaning.

*Flower size.*—An average of 4.3 cm in depth and 4.7 cm in diameter.

*Flower fragrance.*—None.

*Flower shape.*—Broad, tubular funnel.

*Flower number.*—Average of 11 per inflorescence.

*Flower aspect.*—Outward.

*Flower bud.*—Obovate in shape, rounded in cross-section, pointed apex, 3.3 cm in height and 1.3 cm in width, color winter; 151A, edges 174A, color when expanding; 54C.

*Flower attachment.*—Pedicellate.

*Petal number.*—5.

*Petal shape.*—Ovate to elliptic.

*Petal color.*—Lower and upper surface when expanding (balloon stage); 54C, lower (outer) surface when fully open; 4D, with 62C along the central axis and 69A, upper (inner) surface when fully open; 62D and 151B, and speckled nectar guides 151A.

*Petal surface.*—Waxy, glabrous, and smooth on both upper and lower surfaces.

*Petal margins.*—Entire, slightly undulate.

*Petal apex.*—Acute to acuminate and notched.

*Petal base.*—Fused.

*Petal size.*—An average of 4.2 cm in length and 2.5 cm in width.

*Sepal number.*—5.

*Sepal shape.*—Narrowly deltate.

*Sepal margin.*—Entire.

*Sepal size.*—1 mm in length and width.

*Sepal surface.*—Glabrous to lightly pubescent.

*Sepal apex.*—Abruptly rounded.

*Sepal base.*—Fused.

*Sepal color.*—Both surfaces 145B on both immature and mature sepals.

*Peduncle.*—An average of 3.2 cm in length and 6 mm in diameter, 144B and 145A in color, strong, surface hairy.

*Pedicels.*—An average of 2.7 cm in length and 2 mm in diameter, glabrous surface, 144B to 145A in color, strong.

Reproductive organs:

*Gynoecium.*—Pistil; 1, stigmas; round in shape, 183A in color, 1 to 1.5 mm in diameter, style; average of 3.4 cm in length, curved at tip, 2D in color and 144C near stigma and base, ovary; 144B in color, covered with pubescence 155C in color.

*Androecium.*—Stamens; 10, anthers; oblong to elliptical in shape, 3 mm in length, 1.5 mm in width, 161C in color; filaments; 155A in color, pollen; 3D in color and moderate in quantity.

*Fruit/seeds.*—Dehiscent, 5 to 6 valved capsules, size is dependent on pollination, average of 5 mm in length and 3 mm in width, color not dehisced; 176A, 156C, and 146A.

It is claimed:

1. A new and distinct cultivar of *Rhododendron* plant named 'HoldenRhodo213' as herein illustrated and described.

* * * * *